(12) United States Patent
Kato

(10) Patent No.: US 8,294,895 B2
(45) Date of Patent: Oct. 23, 2012

(54) FIRE DETECTOR

(75) Inventor: Kenichi Kato, Tokyo (JP)

(73) Assignee: Nohmi Bosai Ltd., Tokyo (JP)

( * ) Notice: Subject to any disclaimer, the term of this patent is extended or adjusted under 35 U.S.C. 154(b) by 306 days.

(21) Appl. No.: 12/731,574

(22) Filed: Mar. 25, 2010

(65) Prior Publication Data
US 2010/0243898 A1 Sep. 30, 2010

(30) Foreign Application Priority Data

Mar. 27, 2009 (JP) ................................. 2009-079915
Mar. 27, 2009 (JP) ................................. 2009-079916

(51) Int. Cl.
*G01N 21/00* (2006.01)
*G01N 15/06* (2006.01)

(52) U.S. Cl. .................... 356/337; 356/338; 250/573

(58) Field of Classification Search .................. None
See application file for complete search history.

(56) References Cited

U.S. PATENT DOCUMENTS

| 3,936,814 | A | * | 2/1976 | Muller-Girard et al. | 340/508 |
| 4,021,792 | A | * | 5/1977 | Ludt et al. | 340/630 |
| 5,021,677 | A | * | 6/1991 | Igarashi et al. | 250/574 |
| 6,107,925 | A | * | 8/2000 | Wong | 340/628 |
| 6,166,648 | A | * | 12/2000 | Wiemeyer et al. | 340/630 |
| 6,396,405 | B1 | * | 5/2002 | Bernal et al. | 340/630 |
| 7,075,445 | B2 | * | 7/2006 | Booth et al. | 340/630 |
| 2002/0011570 | A1 | * | 1/2002 | Castleman | 250/339.15 |

FOREIGN PATENT DOCUMENTS

JP 2008 082709 4/2008

* cited by examiner

*Primary Examiner* — Michael P Stafira
(74) *Attorney, Agent, or Firm* — Frost Brown Todd LLC

(57) ABSTRACT

Provided is a fire detector in which an element substrate can be easily removed from and mounted into an optical case. The fire detector includes: an optical case (21); an element substrate (31), on which a light-receiving element (12) is mounted, the element substrate (31) being provided in the optical case (21); a signal line (35) passing through an introduction portion of a peripheral wall (21*a*) of the optical case (21), the signal line (35) being connected to the element substrate (31); and an optical cover (30) for closing an opening of the optical case (21), in which the signal line (35) is inserted into a slit (37) which is open on an upper end surface (21*f*) of the introduction portion of the peripheral wall (21*a*).

10 Claims, 5 Drawing Sheets

FIRE DETECTOR

BACKGROUND OF THE INVENTION

1. Field of the Invention

The present invention relates to a fire detector such as a flame detector and a smoke detector.

2. Description of the Related Art

A smoke detector is provided in a fire monitoring area such as a house or a building. A conventional smoke detector includes a first element substrate having a light-emitting element and a second element substrate having a light-receiving element, which are provided inside a casing (also referred to as an "optical case"). A main substrate including a power supply circuit, a current control circuit, an MPU, and the like is provided in a case. Electrical connection for transmission/reception of a signal and power feeding between the first and second element substrates and the main substrate is made through a signal line. The signal line connected to the first and second element substrates passes through a circular hole provided through a peripheral wall of the casing to extend along an outer surface of the peripheral wall so as to be connected to the main substrate (for example, see Japanese Patent Application Laid-open No. 2008-082708; hereinafter, referred to as Patent Document 1).

For inspecting and repairing the smoke detector described above, the first and second element substrates are required to be removed from and replaced into the casing. The signal line is introduced into the circular hole, and hence the signal line is required to be disconnected from the first and second element substrates so as to remove the first and second element substrates from the casing. Moreover, after the first and second element substrates are replaced in the casing, the first and second element substrates and the signal line are required to be connected to each other again. Much efforts are required to remove the element substrates from the casing and to replace the element substrates in the casing in the prior art as described above, and hence operating efficiency is lowered.

Further, in the conventional smoke detector described above, the signal line is provided from the hole formed through the peripheral wall of the casing to the main substrate without being shielded. Therefore, a noise component present inside the casing adversely affects an output of the signal line to result in malfunction of the smoke detector in some cases.

SUMMARY OF THE INVENTION

In view of the problems described above, the present invention has an object to provide a fire detector in which an element substrate can be easily removed from and mounted into an optical case.

In view of the problems described above, the present invention has another object to provide a fire detector with improved shielding effects for a signal line so that the signal line is not affected by a noise component.

According to the present invention, a fire detector includes: an optical case; an element substrate, on which a light-receiving element is mounted, the element substrate being provided in the optical case; a signal line passing through an introduction portion of a peripheral wall of the optical case, the signal line being connected to the element substrate; and an optical cover for closing an opening of the optical case, in which the signal line is inserted into a slit in connection with an upper end surface of the introduction portion of the peripheral wall.

According to the present invention, a fire detector includes: an optical case; a light-receiving element provided in the optical case; a received-light amplifying section for amplifying an output signal of the light-receiving element; and a fire determination section for determining occurrence of a fire when a detection level obtained by A/D conversion of the amplified output signal is equal to or higher than a threshold value, in which: a signal line is connected to an element substrate on which the light-receiving element is mounted; and the signal line passes through a slit formed through a peripheral wall of the optical case.

According to the present invention, a fire detector includes: an optical case whose interior forms a dark box; an air passage constituting a smoke detection portion, for letting a gas flow into the optical case; a light-emitting element provided in the optical case; a light-receiving element for receiving scattered light generated by scattering of light emitted from the light-emitting element by smoke particles present in the smoke detection portion; a received-light amplifying circuit for amplifying an output signal of the light-receiving element; and a fire determination section for determining occurrence of a fire when a detection level obtained by A/D conversion of the amplified output signal is equal to or higher than a threshold value, in which: a signal line is connected to an element substrate on which one of the light-emitting element and the light-receiving element is mounted; and the signal line passes through a slit formed through a peripheral wall of the optical case.

According to the present invention, in the fire detector, a light-shielding wall is provided in a space for housing the signal line in the optical case between a position at which the element substrate is to be mounted and the slit.

According to the present invention, in the fire detector, the slit obliquely intersects the peripheral wall.

According to the present invention, a fire detector includes: an optical case; an element substrate, on which a light-receiving element is mounted, the element substrate being provided in the optical case; a signal line passing through an introduction portion of a peripheral wall of the optical case, the signal line being connected to the element substrate; and an optical cover for closing an opening of the optical case, in which: an outer surface of the optical case and an outer surface of the optical cover have conductivity; and the signal line is held in contact with an outer surface of a peripheral wall by a signal-line retaining portion.

According to the present invention, a fire detector includes: an optical case; a light-receiving element provided in the optical case; a received-light amplifying section for amplifying an output signal of the light-receiving element; and a fire determination section for determining occurrence of a fire when a detection level obtained by A/D conversion of the amplified output signal is equal to or higher than a threshold value, in which: an outer surface of the optical case has conductivity; and a signal-line retaining portion for bringing a signal line connected to an element substrate, on which the light-receiving element is mounted, into contact with the outer surface is provided to the optical case.

According to the present invention, a fire detector includes: an optical case whose interior forms a dark box; an air passage constituting a smoke detection portion, for letting a gas flow into the optical case; a light-emitting element provided in the optical case; a light-receiving element for receiving scattered light generated by scattering of light emitted from the light-emitting element by smoke particles present in the smoke detection portion; a received-light amplifying circuit for amplifying an output signal of the light-receiving element; and a fire determination section for determining occurrence of a fire when a detection level obtained by A/D conversion of the amplified output signal is equal to or higher than a threshold value, in which: an outer surface of the optical case has conductivity; and a signal-line retaining portion for bringing a signal line connected to an element substrate, on which the light-receiving element is mounted, into contact with the outer surface is provided to the optical case.

According to the present invention, in the fire detector, the signal-line retaining portion is provided to an optical cover mounted onto the optical case.

The present invention has the structure as described above, and hence the signal line connected to the element substrate externally extends while being held in the slit provided through the peripheral wall of the optical case. Therefore, the effort of disconnecting the signal line from and reconnecting the signal line to the element substrate can be saved.

Moreover, the light-shielding wall is provided at the position between the position where the element substrate is to be mounted and the slit, and hence the light-receiving element is not adversely affected even if outside light enters the optical case through the slit.

The present invention has the structure as described above, and hence the signal line can be reliably shielded. Thus, the signal line is not affected by the noise component present in the optical case. Accordingly, in contrast to the prior art, the occurrence of malfunction due to the noise component can be prevented according to the present invention.

DETAILED DESCRIPTION OF THE PREFERRED EMBODIMENTS

Figure 1:
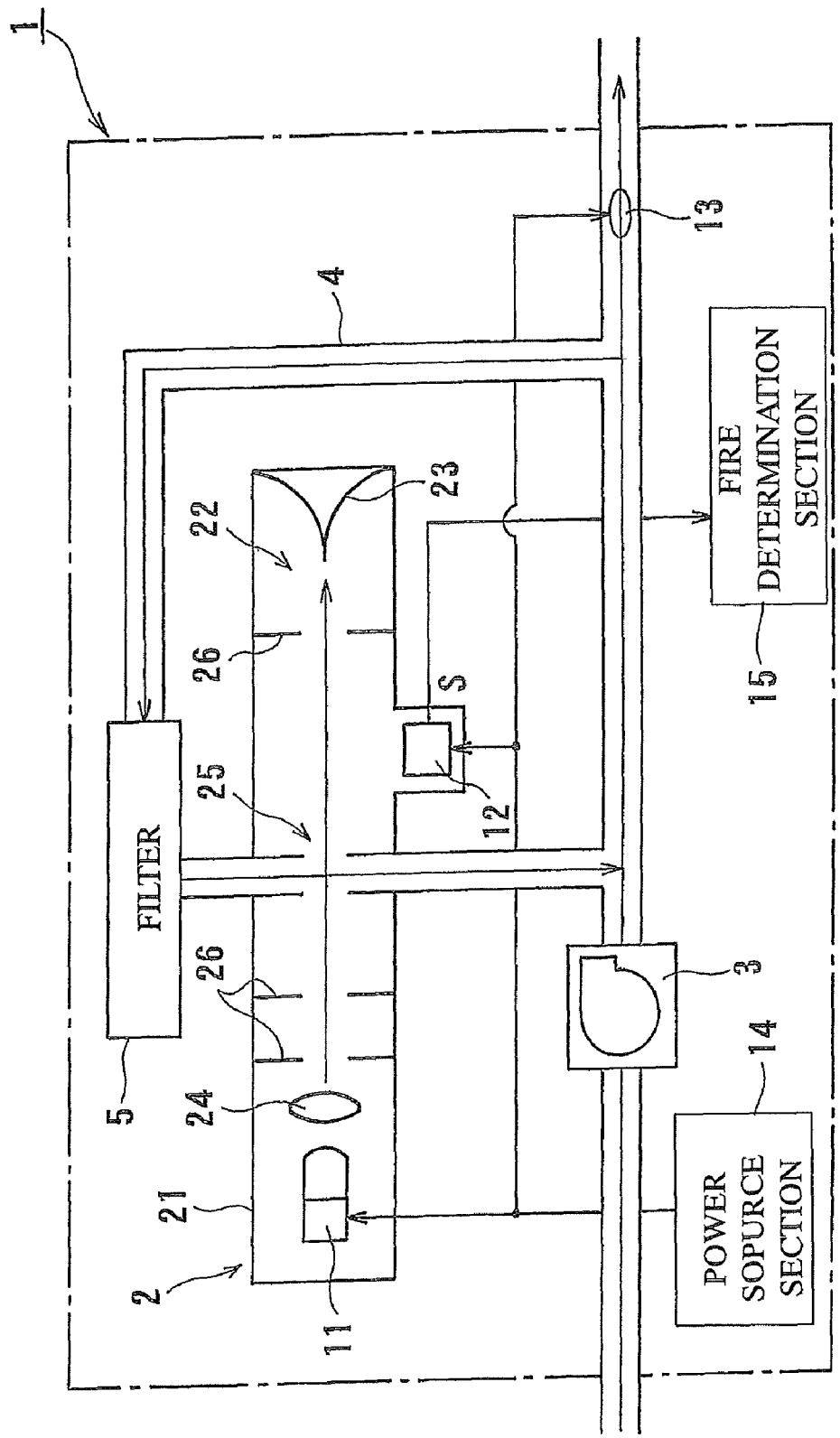
FIG. 1 is a plan view illustrating a first embodiment of the present invention, which shows the schema of a smoke detector.
Figure 2:
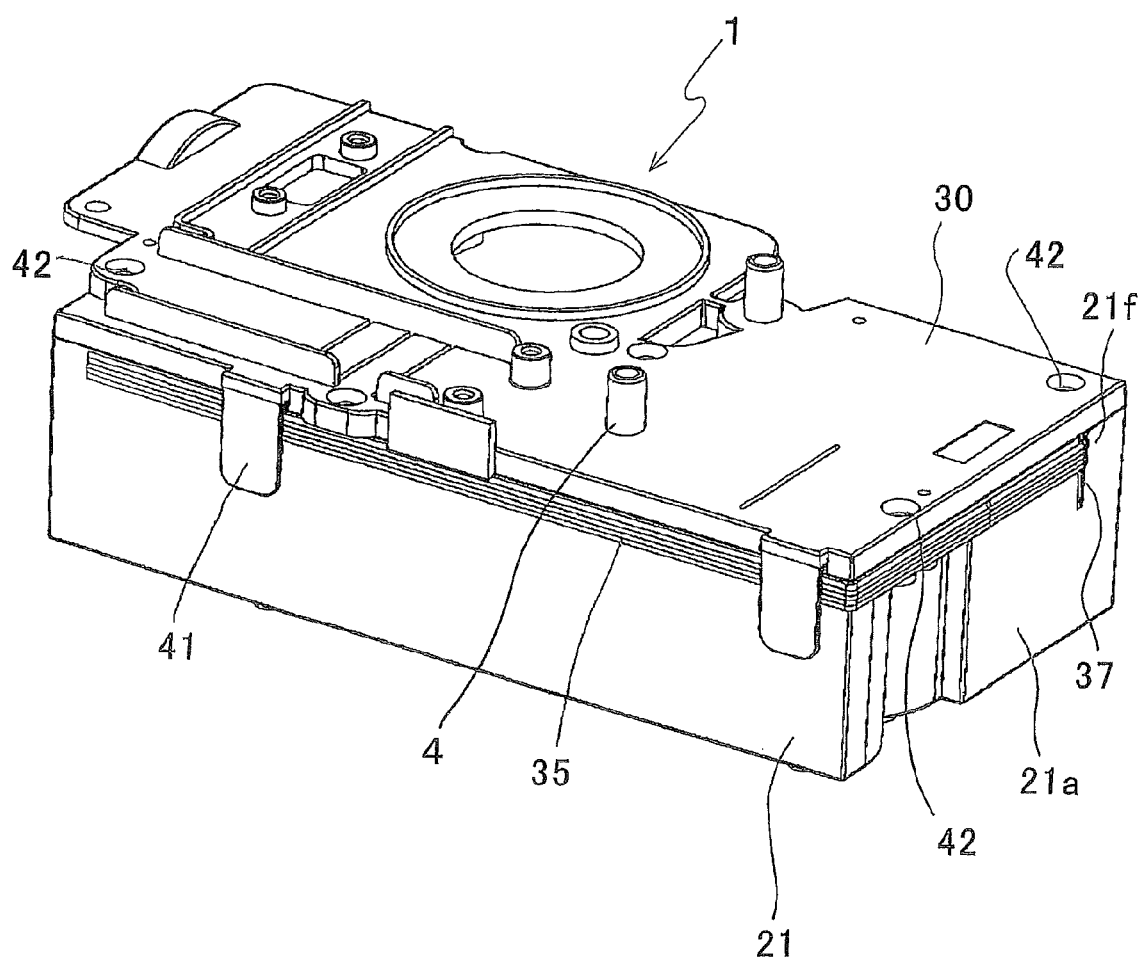
FIG. 2 is a perspective view illustrating a smoke detection unit.
Figure 3:
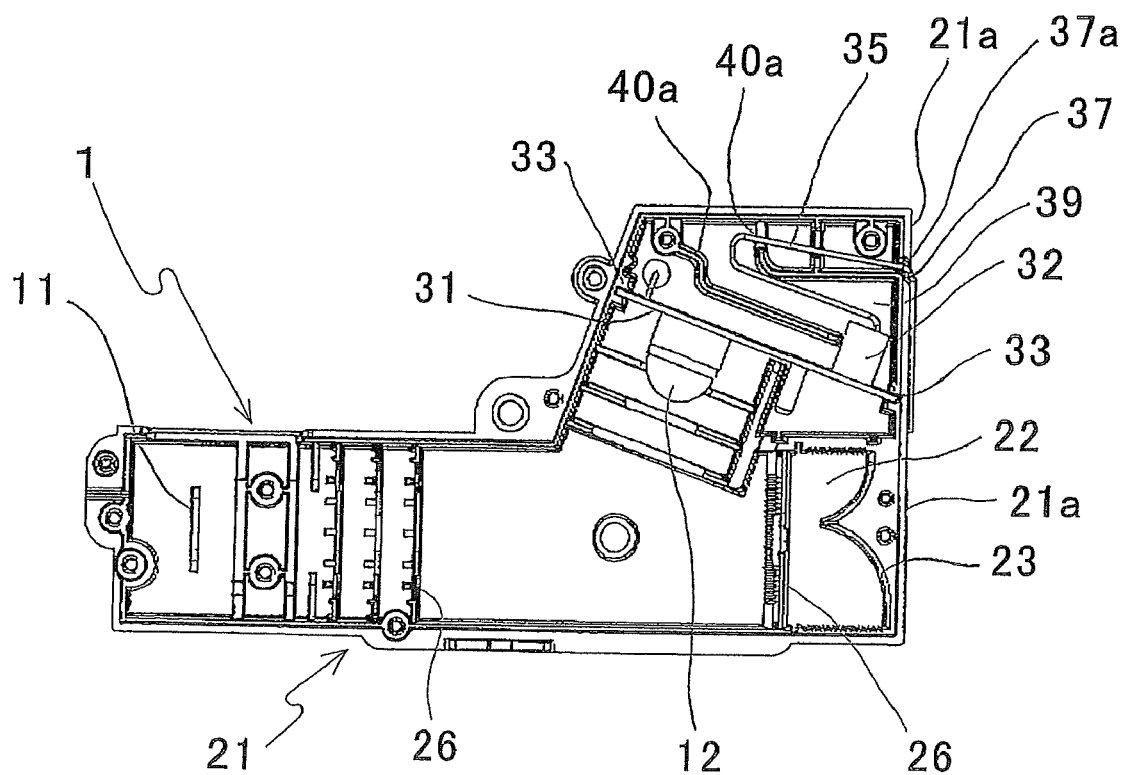
FIG. 3 is a plan view of an optical case.
Figure 4:
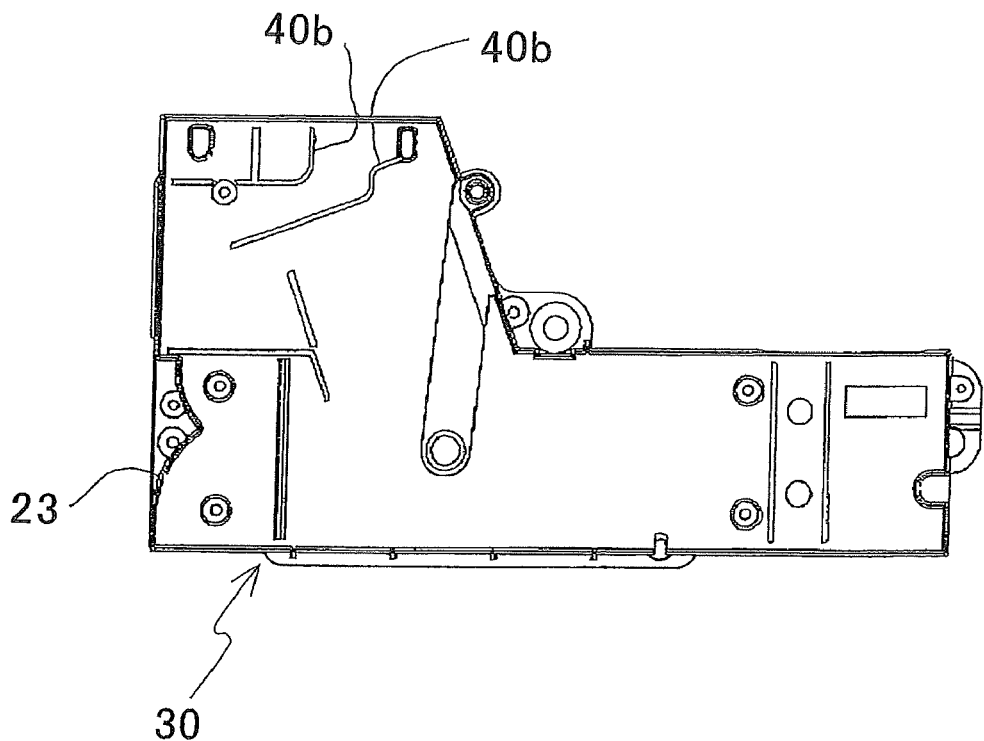
FIG. 4 is a bottom view of an optical cover.
Figure 5:
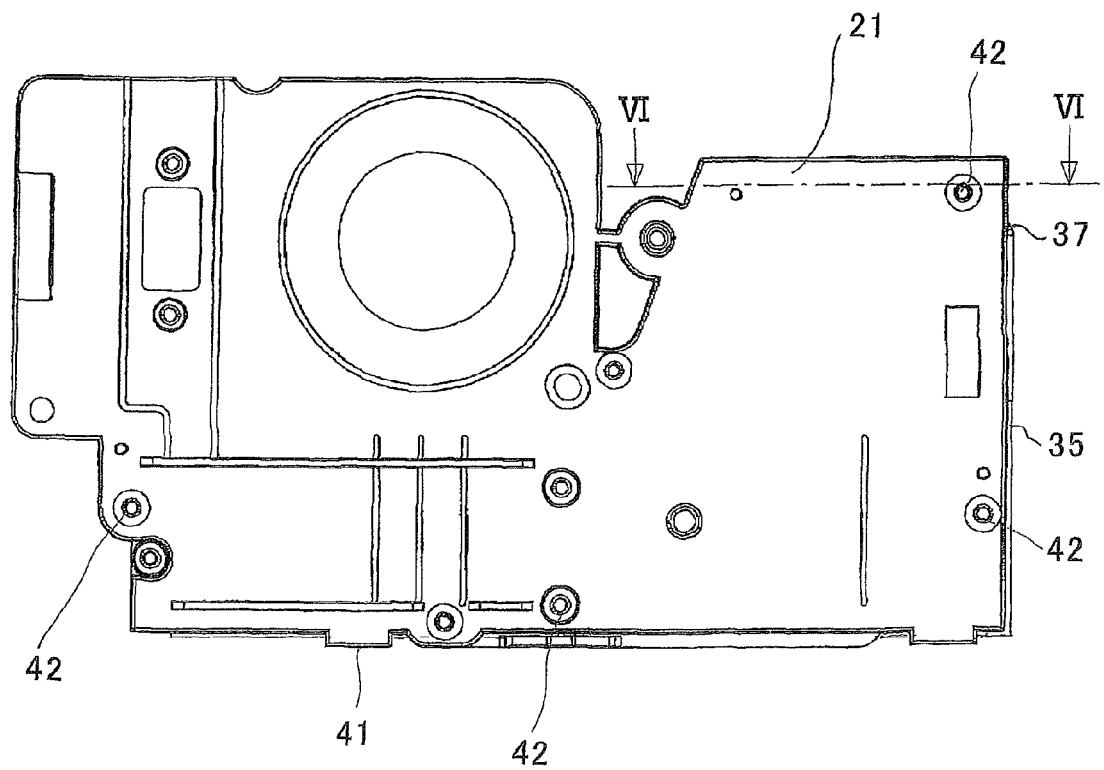
FIG. 5 is a plan view of the smoke detection unit.
Figure 6:
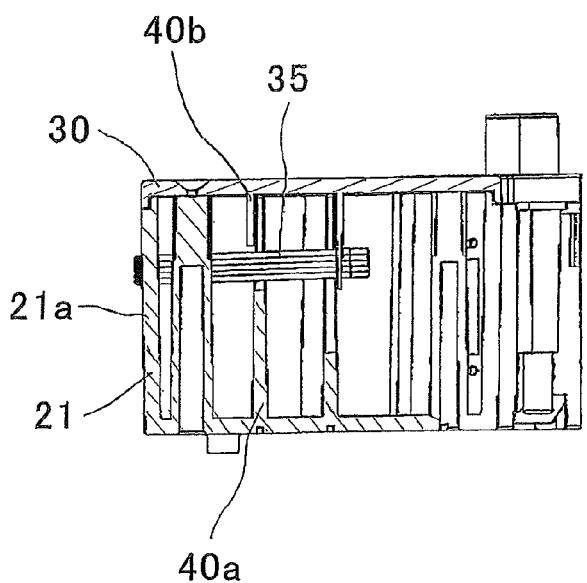
FIG. 6 is a sectional view taken along the line VI-VI of FIG. 5.
Figure 7:
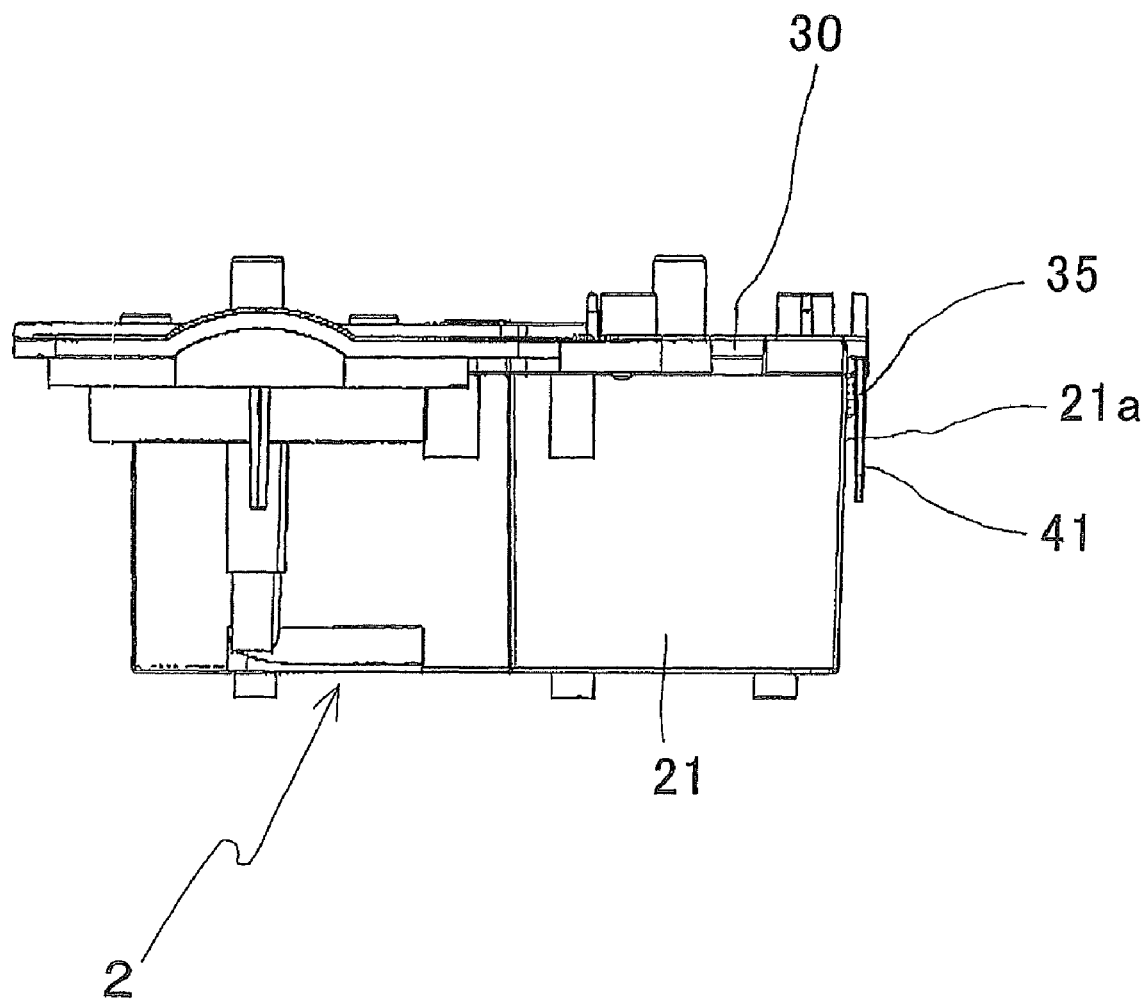
FIG. 7 is a side view of the smoke detection unit.

A smoke detector according to a first embodiment of the present invention is described referring to FIGS. 1 to 7.

The smoke detector 1 includes: a smoke detection unit 2; an optical case 21 of the smoke detection unit 2; a fan 3; and a filter 5. The interior of the optical case 21 forms a dark box. The fan 3 sends the air, which is to be detected, to a smoke detection portion 25 provided in the optical case 21 through a pipe 4. The filter 5 is provided to the pipe 4.

A light-emitting element 11 is provided inside the optical case 21. The light-emitting element 11 is, for example, an element which emits an infrared ray. A light-receiving element 12 such as a photodiode receives scattered light generated by scattering of the light emitted from the light-emitting element 11 by smoke particles present in the smoke detection portion 25. The light-receiving element 12 is provided at a position onto which the light emitted from the light-emitting element 11 is not directly incident. A power source section 14 feeds electric power to the fan 3 and an airflow sensor 13 for measuring an airflow quantity. A fire determination section 15 is also provided.

Although not shown in detail, the fire determination section 15 includes: an amplifier circuit for amplifying an output signal S of the light-receiving element 12; an A/D converter for converting the amplified output signal to a detection level; a comparator circuit for determining the occurrence of a fire when the detection level becomes equal to or higher than a preset threshold value, and the like. Collective control of the fire determination section 15 is performed by a CPU.

The smoke detection unit 2 includes the box-like optical case 21. An opening of the optical case 21 is closed by an optical cover 30. Although an outer surface of the optical case 21 has conductivity because the outer surface of the optical case 21 is subjected to a conductive treatment (such as coating or vapor deposition) so as to block an electromagnetic wave from entering the smoke detection unit 2 from the exterior, the optical case 21 may be formed of an electrically conductive resin instead of the implementation of the conductive treatment. The inner side of the optical case 21 is, for example, mat black, and the interior thereof forms the so-called dark box. A stray-light portion 22 is provided in the optical case 21 so as to be opposed to the light-emitting element 11.

A collective lens 24 collects the light emitted from the light-emitting element 11 on a curved portion of a light trap 23 provided in the stray-light portion 22. The smoke detection portion 25 allows the air to pass therethrough. Apertures 26 are provided at appropriate intervals.

The light-receiving element 12 is mounted on an element substrate 31 along with a circuit component 32. Right and left ends of the element substrate 31 are fitted into grooves 33 so as to be supported thereby. The grooves 33 are concave portions formed on an inner side of a peripheral wall 21a of the optical case 21 so as to vertically extend. Therefore, the element substrate 31 is allowed to be easily inserted and mounted into and removed from the optical case 21 by vertically reciprocating the element substrate 31.

A signal line 35 is connected to the element substrate 31. The signal line 35 is, for example, a band-like flat cable, and is used for the transmission/reception of a signal, power feeding, and the like between the element substrate 31 and a control board (not shown). The signal line 35 exit the optical case 21 through a slit 37 so as to extend along an outer surface of the peripheral wall 21a of the optical case 21.

The slit 37 is formed so as to obliquely intersect the peripheral wall 21a. In this manner, the signal line 35 is bent so as to more easily extend along the outer surface of the peripheral wall 21a and outside light is less likely to enter the optical case 21, as compared with the case where the slit is provided so as to orthogonally intersect the peripheral wall. Further, the signal line 35 is lightly held in the slit 37, and hence a part of the signal line 25, which is located inside the optical case 21, is not affected even if the signal line 35 is pulled from the exterior of the optical case 21. Moreover, an opening 37a of the slit 37 is in connection with (is open on) an upper end surface 21f of the peripheral wall 21a. In this manner, mere vertical reciprocating movement of the signal line 35 enables the signal line 35 to be placed in and removed from the slit 37. Therefore, the element substrate 37 can be removed from or inserted and mounted into the optical case 21 while the signal line 35 is being connected to the element substrate 31.

A housing section 39 for the signal line is provided between the element substrate 31 and the slit 37 in the optical case 21. Light-shielding walls 40 are provided in the housing section 39. The light-shielding walls 40 include light-shielding walls 40a fixed to the optical case 21 and light-shielding walls 40b fixed to the optical cover 30. As a whole, the light-shielding walls 40 are provided along a path of the signal line 35 to surround the path of the signal line 35 so that the outside light does not reach the element substrate 31. Further, the light-shielding walls 40a and 40b are provided so as to be adjacent to each other to enhance light-shielding effects.

On an opening of the optical case 21, the optical cover 30 is placed so as to cover the opening. The optical cover 30 is fixed to the optical case 21 by screws 42. Although an outer surface of the optical cover 30 has conductivity because the outer surface of the optical cover 30 is subjected to the conductive treatment (such as coating or vapor deposition) so as to block an electromagnetic wave from entering the smoke detection unit 2 from the exterior, the optical cover 30 may be formed of an electrically conductive resin instead of the implementation of the conductive treatment. On longer-side edges of the optical cover 30, a plurality of signal-line retaining portions 41 are provided at a distance from each other. The signal-line retaining portions 41 are pressure-support members for retaining the band-like signal line 35 so that the signal line 35 is held in contact with the peripheral wall 21a of the optical case 21. The signal-line retaining portions 41 are plate-like pieces which extend downward from the longer-side edges of the optical cover 30.

A length of each of the signal-line retaining portions 41 is set so as to be longer than a band width of the signal line 35, and is set to be, for example, approximately the same as a length (depth) of the slit 37. Further, a distance between an inner surface of each of the signal-line retaining portions 41 and the outer surface of the peripheral wall 21a is set so as to be slightly smaller than a thickness of the signal line 35 (a length of the signal line 35, which is perpendicular to the band width). In this manner, the signal-line retaining portions 41 are capable of supporting the signal line 35 in a pressurized manner. The number, the band width, and the length of the signal-line retaining portions 41 are appropriately selected as needed. Note that, as in the case of the optical cover 30, the signal-line retaining portions 41 may be provided with conductivity.

Note that, mounting bosses for the substrate and board all have a grounding function and are grounded on vapor-deposited surfaces of the bosses and a surface of a land on a bottom surface of each of the substrate and board. Moreover, by providing the bosses for mounting the substrate and board to the optical case 21 and the optical cover 30, a potential of the optical case 21 and that of the optical cover 30 can be made equal to each other through the ground of each of the substrate and board. Therefore, by bringing the signal line 35, and the outer surface of the optical case 21 and the outer surface of the optical cover 30 close to each other, an electrostatic capacitance is generated between the signal line 35 and the outer surfaces of the optical case 21 and the optical cover 30. As a result, noise resistance is enhanced.

An operation of the smoke detector of this embodiment is now described.

The outer surface of the optical case 21 and the outer surface of the optical cover 30 have the conductivity, while the signal line 35 is held in contact with the peripheral wall 21a of the optical case 21. Thus, the signal line 35 is in a shielded state. Accordingly, the signal line 35 is not affected by noise present in the optical case 21, and hence the fire determination section 15 can make a normal determination. Thus, the malfunction of the fire detector can be prevented.

For removing the element substrate 31 placed in the smoke detection unit 2 from the optical case 21, the screws 42 are loosened to detach the optical cover 30 from the optical case 21. Then, the interior of the optical case 21 is exposed, whereas the upper ends of the grooves 33 and the upper end (opening 37a) of the slit 37 of the optical case 21 are brought into an open state.

When the element substrate 31 and the signal lines 35, which are placed in the optical case 21, are pulled up with fingers, the element substrate 31 is pulled out of the grooves 33 while the signal line 35 is pulled out of the slit 37. Therefore, the element substrate 31 can be easily removed from the optical case 21 while being connected to the signal line 35.

For mounting the element substrate 31 into the optical case 21, a mounting operation is performed in reverse order of the above-mentioned removal operation. Specifically, while the element substrate 31 and the signal line 35 are in connection with each other, the element substrate 31 is moved downward so as to be pressed into the groove 33. At the same time, the signal line 35 is moved downward so as to be pressed into the opening 37a of the slit 37. As a result, the element substrate 31 and the signal line 35 are located at the respective design positions. In addition, the signal line 35 is lightly held in the slit 37. At this time, the part of the signal line 35, which is located inside the optical case 21, is housed along the formed path.

The signal line 35 is led to the predetermined position so as to extend along the outer surface of the peripheral wall 21a. Thereafter, the optical case 30 is placed on the opening of the optical case 21. After the signal line 35 is brought into contact with the peripheral wall 21a by the signal-line retaining portions 41, the optical cover 30 is fixed to the optical case 21 by the screws 42. At this time, the depth of the slit 37 or a height of a stopper of the optical cover 30 may be set so as to limit the vertical movement of the signal line 35 in the opening 37a of the slit 37.

A second embodiment of the present invention is now described (not shown).

The fire detector of the present invention can be applied not only to the smoke detector but also to a fire detector (for example, a flame detector) which does not include the light-emitting element.

Specifically, the fire detector according to the second embodiment includes: a box-like optical case; a light-receiving element provided in the optical case; a received-light amplifying section for amplifying an output signal of the light-receiving element; a fire determination section for determining the occurrence of a fire when a detection level obtained by A/D conversion of the amplified output signal is equal to or higher than a threshold value; and an optical cover mounted onto the optical case. The optical case has the outer surface with conductivity and the signal-line retaining portions for bringing the signal line connected to the element substrate, on which the light-receiving element is mounted, into contact with the outer surface.

The signal line is connected to the element substrate on which the light-receiving element is mounted. The signal line is provided so as to pass through a slit formed through a peripheral wall of the optical case.

Note that, the optical cover, the optical case, the slit, and the signal-line retaining portions are the same as those of the first embodiment.

What is claimed is:
1. A fire detector, comprising:
an optical case;
a light-receiving element provided in the optical case;
a received-light amplifying section for amplifying an output signal of the light-receiving element; and
a fire determination section for determining occurrence of a fire when a detection level obtained by A/D conversion of the amplified output signal is equal to or higher than a threshold value, wherein:
a signal line is connected to an element substrate on which the light-receiving element is mounted; and
the signal line passes through a slit formed obliquely through a peripheral wall of the optical case wherein the signal line passes through said slit so that said signal line is bent more easily extend along the outer surface of said peripheral wall and to have outside light less likely to enter said optical case.

2. A fire detector, comprising:
an optical case whose interior forms a dark box;
an air passage constituting a smoke detection portion, for letting a gas flow into the optical case;
a light-emitting element provided in the optical case;
a light-receiving element for receiving scattered light generated by scattering of light emitted from the light-emitting element by smoke particles present in the smoke detection portion;
a received-light amplifying circuit for amplifying an output signal of the light-receiving element; and
a fire determination section for determining occurrence of a fire when a detection level obtained by A/D conversion of the amplified output signal is equal to or higher than a threshold value, wherein:
a signal line is connected to an element substrate on which one of the light-emitting element and the light-receiving element is mounted; and
the signal line passes through a slit formed obliquely through a peripheral wall of the optical case wherein the signal line passes through said slit so that said signal line is bent more easily extend along the outer surface of said peripheral wall and to have outside light less likely to enter said optical case.

3. A fire detector according to claim 1, wherein a light-shielding wall is provided in a space for housing the signal line in the optical case between a position at which the element substrate is to be mounted and the slit.

4. A fire detector according to claim 2, wherein a light-shielding wall is provided in a space for housing the signal line in the optical case between a position at which the element substrate is to be mounted and the slit.

5. A fire detector according to claim 1, wherein the slit obliquely intersects the peripheral wall.

6. A fire detector according to claim 2, wherein the slit obliquely intersects the peripheral wall.

7. A fire detector, comprising:
an optical case;
a light-receiving element provided in the optical case;
a received-light amplifying section for amplifying an output signal of the light-receiving element; and
a fire determination section for determining occurrence of a fire when a detection level obtained by A/D conversion of the amplified output signal is equal to or higher than a threshold value, wherein:
an outer surface of the optical case has conductivity;
a signal-line retaining portion for bringing a signal line connected to an element substrate, on which the light-receiving element is mounted, into contact with the outer surface is provided to the optical case so that said signal line is not affected by noise present in said optical case; and
an opening of the optical case is closed by an optical cover having conductivity.

8. A fire detector, comprising:
an optical case whose interior forms a dark box;
an air passage constituting a smoke detection portion, for letting a gas flow into the optical case;
a light-emitting element provided in the optical case;
a light-receiving element for receiving scattered light generated by scattering of light emitted from the light-emitting element by smoke particles present in the smoke detection portion;
a received-light amplifying circuit for amplifying an output signal of the light-receiving element; and
a fire determination section for determining occurrence of a fire when a detection level obtained by A/S conversion of the amplified output signal is equal to or higher than a threshold value, wherein:
an outer surface of the optical case has conductivity;
a signal-line retaining portion for bringing a signal line connected to an element substrate, on which the light-receiving element is mounted, into contact with the outer surface is provided to the optical case so that said signal line is not affected by noise present in said optical case; and
an opening of the optical case is closed by an optical cover having conductivity.

9. A fire detector according to claim 7, wherein the signal-line retaining portion is provided to the optical cover mounted onto the optical case.

10. A fire detector according to claim 8-, wherein the signal-line retaining portion is provided to the optical cover mounted onto the optical case.

* * * * *